United States Patent

Daley

Patent Number: 5,902,319
Date of Patent: May 11, 1999

[54] BIOABSORBABLE STAPLES

[76] Inventor: Robert J. Daley, 10611 Wild Flower Rd., Orland Park, Ill. 60462

[21] Appl. No.: 08/937,414

[22] Filed: Sep. 25, 1997

[51] Int. Cl.$^6$ .................................................... A61B 17/00
[52] U.S. Cl. ............................................................ 606/219
[58] Field of Search ..................... 606/219, 151, 606/53, 75, 220, 221, 60, 22, 99, 77, 154; 623/13

[56] References Cited

U.S. PATENT DOCUMENTS

| | | |
|---|---|---|
| 3,625,220 | 12/1971 | Engelsher . |
| 4,534,350 | 8/1985 | Golden et al. . |
| 4,534,352 | 8/1985 | Korthoff . |
| 4,612,923 | 9/1986 | Kronenthal . |
| 4,635,637 | 1/1987 | Schreiber ................................ 606/219 |
| 4,646,741 | 3/1987 | Smith . |
| 4,889,119 | 12/1989 | Jamiolkowski et al. . |
| 4,950,285 | 8/1990 | Wilk . |
| 5,123,913 | 6/1992 | Wilk et al. . |
| 5,209,756 | 5/1993 | Seedhom et al. ....................... 606/151 |
| 5,282,829 | 2/1994 | Hermes . |
| 5,439,479 | 8/1995 | Shichman et al. . |
| 5,462,542 | 10/1995 | Alesi, Jr. . |
| 5,489,287 | 2/1996 | Green et al. ............................ 606/139 |
| 5,549,619 | 8/1996 | Peters et al. . |
| 5,550,000 | 8/1996 | Feagin et al. .......................... 606/232 |
| 5,601,604 | 2/1997 | Vincent . |
| 5,643,295 | 7/1997 | Yoon . |
| 5,693,023 | 12/1997 | Adams ................................... 606/195 |

OTHER PUBLICATIONS

Pavletic et al., Veterinary Clinics of North America: Small Animal Practice, vol. 24, No. 2, pp. 247–278, Mar. 1994.

Von Fraunhofer, Legating Clips and Staples, in Wound Closure Biomaterials and Devices, Chu et al., Eds., pp. 307–316, CRC Press, 1997.

*Primary Examiner*—Michael Buiz
*Assistant Examiner*—Vikki Trinh
*Attorney, Agent, or Firm*—Bell, Boyd & Lloyd

[57] ABSTRACT

The present invention reveals bioabsorbable staples and methods for tissue closure. The first type of staple is a one-piece bioabsorbable staple constructed of an elongate body and a locking mechanism, where the locking mechanism is made up of a retainer having a central tunnel and is located at the first end of the elongate body, and an arrow head located at the second end of the elongate body. The second type of staple is a two-piece staple for tissue closure constructed of a first elongate body having a leg connected to an arrow head at each end and a second elongate body having a retainer at each end, where each retainer contains an eyelet. Each method for tissue closure involves grasping and holding the tissue to be closed, forcing a bioabsorbable staple through the tissue, and locking the staple.

6 Claims, 3 Drawing Sheets

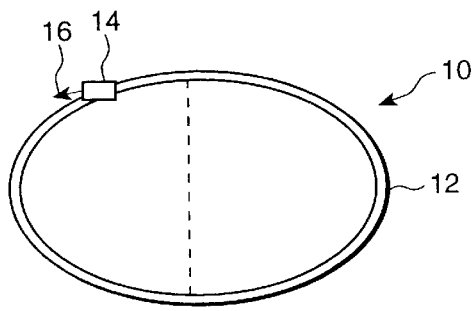
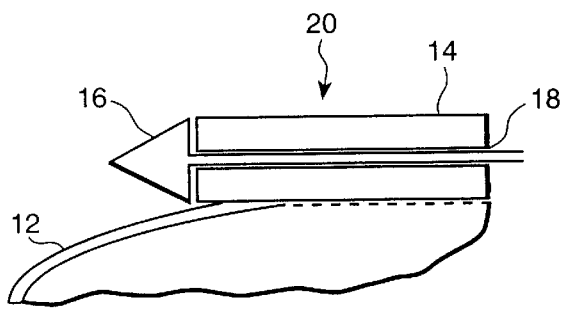
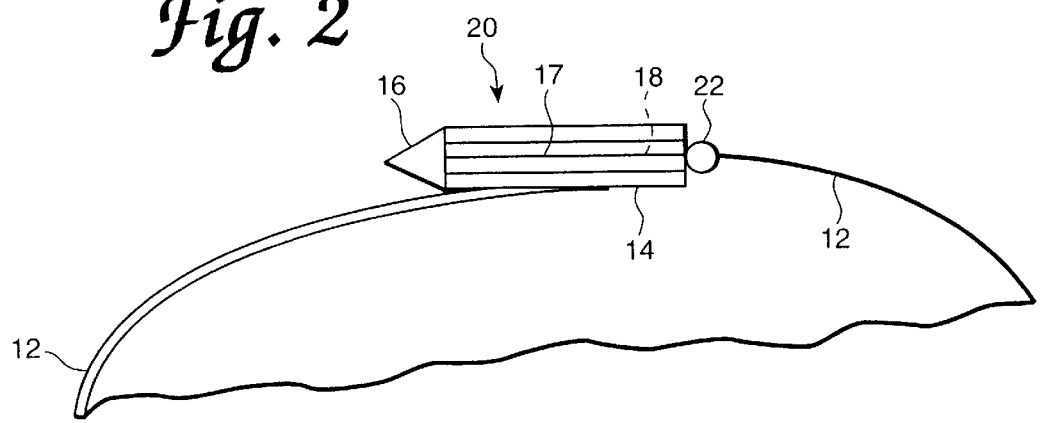
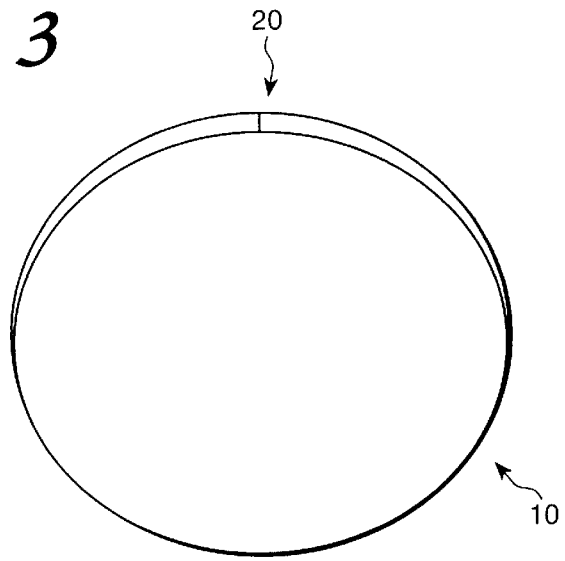

BIOABSORBABLE STAPLES

BACKGROUND OF THE INVENTION

1. Field of the Ivention

The present invention discloses new bioabsorbable staples and methods for tissue closure. These bioabsorbable staples improve the consistency and reliability of the suturing process, and facilitate the wound closure process. The staples are delivered through a separate staple delivery device.

The first type of bioabsorbable staple is comprised of a single piece. The one-piece staple has three parts, namely, an elongated body, a retainer at one end of the elongated body, and an arrow head at the other end of the elongated body. The retainer has a tunnel passing through its core. The arrow head is inserted through the tunnel of the retainer and forms a secure lock with the retainer. The secured arrow head, retainer, and elongated body form a closed ellipsoid suture structure.

The other type of bioabsorbable staple is comprised of two pieces. The two-piece staple or suture is comprised of a first elongated body having a leg connected to an arrow head at each end and a second elongated body having a retainer at each end, where each retainer contains an eyelet. The arrow heads are separately inserted into the eyelets of the retainers. The secured arrow heads, retainers, and elongated bodies form a closed ellipsoid suture structure.

2. Description of the Related Art

Because of the advantages over conventional suturing techniques, mechanical stapling is now widely used in surgical procedures. Wound closure with stainless steel staples has resulted, for example, in decreased tissue trauma, a reduction in the length of hospital stay, and a lower infection rate (see, for example, Steckel et al., Experimental Evaluation of Absorbable Copolymer Staples for Hysterectomy, *Obstetrics & Gynecology*, Vol. 68, No.3, pp. 404–410, September 1986).

Numerous types of surgical staples have been reported. For example, U.S. Pat. No. 3,625,220 (Engelsher) discloses a suture guard device comprised of an outer tube, an inner tube, and a locking means. The suture guard is semirigid and preferably made of polyethylene.

U.S. Pat. No. 4,534,350 (Golden et al.) discloses a two-piece tissue fastener comprised of an open loop fastening member having two legs with rows of rounded protrusions and a receiver. The legs of the fastening member are inserted into bores of the receiver and the rounded protrusions cooperate with a bore to form a secure connection.

Both U.S. Pat. No. 4,950,285 (Wilk) and U.S. Pat. No. 5,123,913 (Wilk et al.) disclose a one-piece suture device comprised of:

a) a thread provided with a series of resilient projections along a portion of its length, b) a loop defining an opening, c) a joining means for connecting one end of the thread to the loop, and d) locking means.

U.S. Pat. No. 5,601,604 (Vincent) discloses a one-piece gastric band comprised of a body portion with a tail end and a buckle. The tail end of the body portion is inserted into the buckle to form a loop.

However, none of these patents disclose bioabsorbable staples and all are patentably distinguishable over the bioabsorbable staples of the present invention. Furthermore, none of these patents are believed to have any direct relevance to the patentability of the bioabsorbable staples of the present invention.

Although the advantages of stapling are numerous, complications associated with the use of steel staples led to the development of bioabsorbable staples.

Bioabsorbable staples were developed by combining different concentrations of lactide and glycolide, polymerized under varying conditions to enhance their rate of hydrolysis and absorption from tissues. In the early 1980s, lactomer absorbable plastic staples, e.g., polysorb, became available for use in hysterectomy in women. Lactomer staples are hard and opaque, and are unlike conventional metallic staples in that they are not bent during their application to form the shape of a "B". Rather, each copolymer staple is composed of two parts: a "U"-shaped fastener and an "8"-shaped retainer. When the stapling instrument is fired, the fastener is forced through the tissue and locks into its retainer. Currently available lactomer staples retain about 75% of their initial strength during the first postoperative week, with 40% tensile strength retention at about 2 weeks. The staples begin fragmenting after 3 to 4 weeks, and absorption follows. Numerous types of bioabsorbable surgical staples have been reported. For example, U.S. Pat. No. 4,534,352 (Korthoff) discloses a two-piece surgical fastener made from an absorbable resinous material. The surgical fastener is comprised of a base and a prong-containing member. Each prong is inserted into an aperture in the base to form a secure connection.

U.S. Pat. No. 4,612,923 (Kronenthal) discloses a two-piece surgical fastener made from a synthetic absorbable polymer containing an absorbable glass filler. The surgical fastener is comprised of a staple and a receiver. The staple is inserted into openings in the receiver to form a secure connection.

U.S. Pat. No. 4,646,741 (Smith) discloses a two-piece surgical staple made from a blend of a lactide/glycolide copolymer and poly(p-dioxanone). The surgical staple is comprised of a base with two legs and a receiver. The legs of the base are inserted into receptacles in the receiver to form a secure connection.

U.S. Pat. No. 4,889,119 (Jamiolkowski et al.) discloses a two-piece surgical fastener made from a glycolide-rich blend of two or more polymers. The surgical fastener is comprised of a base with two legs and a receiver. The legs of the base are inserted into receptacles in the receiver to form a secure connection.

U.S. Pat. No. 5,282,829 (Hermes) discloses a two-piece biodegradable surgical device comprised of a fastener with two prongs and a receiver. The prongs of the fastener are inserted into the receiver to form a secure connection. Both the fastener and the receiver contain a hollow core region.

U.S. Pat. No. 5,439,479 (Shichman et al.) discloses a biodegradable two-piece surgical clip comprised of a fastener and a retainer. The fastener has a set of legs containing gripping means adapted to be engaged by the retainer. When the legs of the fastener are engaged by the retainer, a closed connection is formed.

U.S. Pat. No. 5,462,542 (Alesi, Jr.) discloses a biodegradable one-piece surgical strap assembly having a flexible elongated strap and a buckle attached to one end of the strap. A portion of the strap contains a plurality of ratchet teeth. The ratchet teeth of the strap engage a locking mechanism in the buckle to form a loop.

U.S. Pat. No. 5,549,619 (Peters et al.) discloses a biodegradable one-piece or two-piece surgical device comprised of an eye with a latching pawl and a flexible strip with ratchet teeth. The ratchet teeth of the flexible strip engage with the latching pawl of the eye to form a loop.

U.S. Pat. No. 5,643,295 (Yoon) discloses an apparatus for suturing tissue comprised of a knotting element connected between two length portions of filamentous suture material to form a contractile loop for confining segments of the length portions therein.

However, each of these patents is patentably distinguishable over the bioabsorbable staples of the present invention and none of these patents are believed to have any direct relevance to the patentability of the bioabsorbable staples of the present invention.

A thorough review of the field of bioabsorbable staples and stapling instrumentation has been reported by Michael M. Pavletic and Anthony Schwartz in *Veterinary Clinics of North America: Small Animal Practice,* Volume 24, Number 2, pages 247–278, March 1994.

SUMMARY OF THE INVENTION

The present invention discloses bioabsorbable staples and methods for tissue closure. The first type of staple is a one-piece staple for tissue closure, comprising:

a) an elongate body, and b) a locking mechanism, where the locking mechanism comprises i) a retainer having a central tunnel and is located or situated at the first end of the elongate body, and ii) an arrow head located or situated at the second end of the elongate body, where the staple is bioabsorbable and forms an ellipsoid structure when the arrow head is inserted into the tunnel of the retainer of the locking mechanism.

In another embodiment of the one-piece staple, the locking mechanism further comprises a locking bead situated on the elongate body behind the arrow head at the second end of the elongate body. When the arrow head is inserted into the tunnel of the retainer of the locking mechanism, the arrow head contacts the first end of the retainer and the locking bead contacts the second end of the retainer.

In another embodiment of the one-piece staple, the locking mechanism further comprises a retainer having an interior ledge at one end of the tunnel. When the arrow head is inserted into the tunnel of the retainer of the locking mechanism, the arrow head engages the interior ledge of the tunnel. In another aspects of this embodiment, the tunnel has a single opening and the interior ledge is located at the end of the tunnel having the opening.

In a most preferred embodiment of the one-piece staple, the ellipsoid structure formed when the arrow head is inserted into the retainer of the locking mechanism has a smooth, tapered, and continuous outer surface, as seen in FIG. 3.

In each of the above-given embodiments, the arrow head may be solid or may be comprised of a hollow outer cone and a shaft which is continuous with the elongate body. In the later embodiment, the hollow cone collapses when passing through the tunnel of the retainer and returns to its original shape when the arrow head is completely inserted through the tunnel of the retainer of the locking mechanism.

The one-piece bioabsorbable staples may be constructed from polydiaxanone, a copolymer of glycolic acid and lactic acid, or a blend of polydiaxanone and a copolymer of glycolic acid and lactic acid. Polydiaxanone is particularly preferred for the construction of the one-piece staple.

The method for tissue closure with the one-piece staple comprises the steps of grasping and holding the tissue to be closed, forcing a one-piece bioabsorbable staple through the tissue, and locking the staple.

In a most preferred embodiment of the method, the one-piece bioabsorbable staple has a smooth, tapered, and continuous outer surface, as seen in FIG. 3.

The one-piece bioabsorbable staples used in the method may be constructed from polydiaxanone, a copolymer of glycolic acid and lactic acid, or a blend of polydiaxanone and a copolymer of glycolic acid and lactic acid. Polydiaxanone is particularly preferred in the method.

The second type of staple is a two-piece staple for tissue closure, comprising:

a) a first elongate body having a leg connected to an arrow head at each end; and b) a second elongate body having a retainer at each end, where each retainer contains an eyelet. In this type of staple, each arrow head of the first elongate body engages with an eyelet of the retainer of the second elongate body. Furthermore, the staple is bioabsorbable and forms an ellipsoid structure when the arrow heads of the first elongate body engage with the eyelets of the retainer of the second elongate body.

With this type of staple, the arrow head is preferably solid and may be constructed from polydiaxanone, a copolymer of glycolic acid and lactic acid, or a blend of polydiaxanone and a copolymer of glycolic acid and lactic acid. A copolymer of glycolic acid and lactic acid is particularly preferred for the construction of the two-piece staple.

The method for tissue closure with the two-piece staple comprises the steps of grasping and holding the tissue to be closed, forcing a two-piece bioabsorbable staple through the tissue, and locking the staple.

For the one-piece staple, the two-piece staple, and the respective methods for tissue closure, the tissue can be selected from the group consisting of fascia, tendon, muscle, and ligament.

BRIEF DESCRIPTION OF THE DRAWINGS

FIG. 1A shows one embodiment of the one-piece bioabsorbable staple of the present invention.

FIG. 1B shows a close up of the retainer and the arrow head of the one-piece bioabsorbable staple of FIG. 1A.

FIG. 2 shows a close up of another embodiment of the arrow head of the one-piece bioabsorbable staple of FIG. 1A.

FIG. 3 shows another embodiment of the one-piece bioabsorbable staple of the present invention.

DETAILED DESCRIPTION OF THE PREFERRED EMBODIMENT

Figure 4:
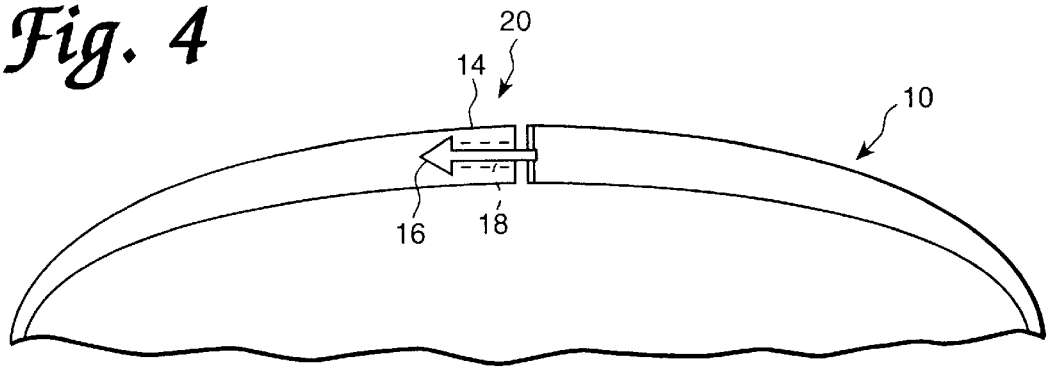
FIG. 4 shows a close up of the retainer and the arrow head of the one-piece bioabsorbable staple of FIG. 3.

The present invention discloses new bioabsorbable staples and methods for tissue closure. The tissue can be selected from the group consisting of fascia, tendon, muscle, and ligament. The present invention is exceptionally suited for fascia closure.

The bioabsorbable staples may be made of any bioabsorbable material such as, for example, polydiaxanone or polysorb, a copolymerized glycolic and lactic acid, or a blend of polydiaxanone and a copolymer of glycolic and lactic acid. The polysorb is also known as lactomer. The staples are used for tissue closure, improve the consistency and reliability of the suturing process, and facilitate the wound closure process. The staples are delivered through a separate staple delivery device.

The first type of bioabsorbable staple is comprised of a single piece. The one-piece staple 10, as seen in FIG. 1A, has three parts, namely, an elongate body 12, a retainer 14 at one end of the elongate body 12, and an arrow head 16 at the other end of the elongate body 12. The retainer 14 has a central tunnel 18 passing through its core, as seen in FIG. 1B. The arrow head 16 is attached to a shaft 17, best seen in FIGS. 2, 7A, and 7B, which is continuous with the elongate body 12. The arrow head 16 is inserted through the tunnel 18 of the retainer 14 and forms a secure lock or locking mechanism 20 with the retainer 14. The secured arrow head 16, retainer 14, and elongate body 12 form a closed ellipsoid staple structure 10. The staples are delivered through a separate staple delivery device.

Figure 6A:
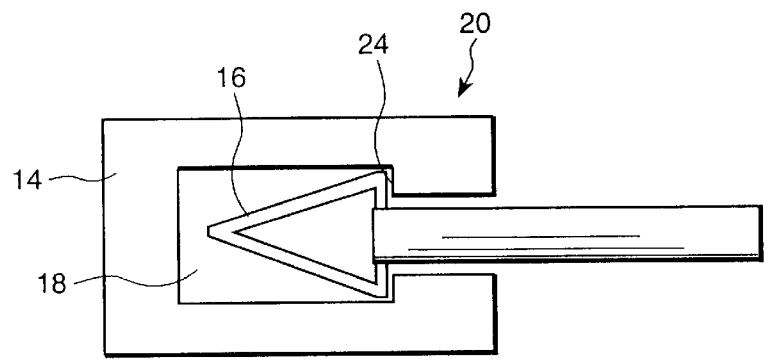
FIGS. 6A and 6B show other embodiments of the locking mechanisms of the present invention.
Figure 6B:
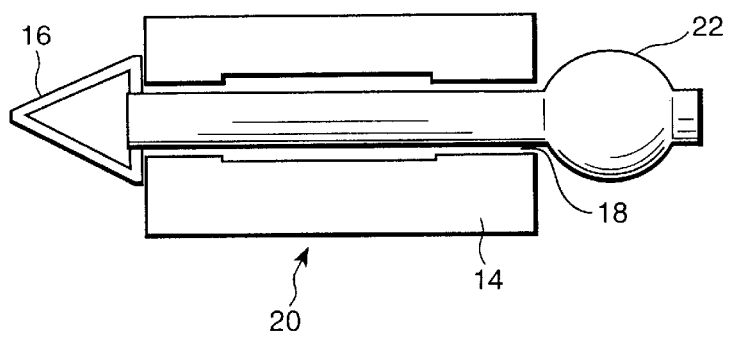

The locking mechanism 20 can be further constructed to contain a locking bead 22 situated behind the arrow head 16 at the second end of the elongate body 12, as seen in FIGS. 2 and 6B. In this embodiment, the arrow head 16 contacts the first end of the retainer 14 and the locking bead 22 contacts the second end of the retainer 14 when the arrow head 16 is inserted into the tunnel 18 of the retainer 14 of the locking mechanism 20.

The locking mechanism 20 can be further constructed to contain a retainer 14 having an interior ledge 24 at one end of the tunnel 18. In this embodiment, seen in FIG. 6A, the arrow head 16 engages the interior ledge 24 of the tunnel 18 when the arrow head 16 is inserted into the tunnel 18 of the retainer 14 of the locking mechanism 20.

In another embodiment, the ellipsoid structure 10 formed when the arrow head 16 is inserted into the retainer 14 of the locking mechanism 20 has a smooth, tapered, and continuous outer surface, as seen in FIG. 3. This same configuration is seen in cross-section in FIG. 4.

More specifically, the locking mechanism 20 is contained within the body of the staple 10 so that the arrow head 16 is buried inside the tunnel 18 of the retainer 14 of the locking mechanism 20. This configuration results in a staple 10 having a smooth, tapered, and continuous outer surface.

Figure 7A:
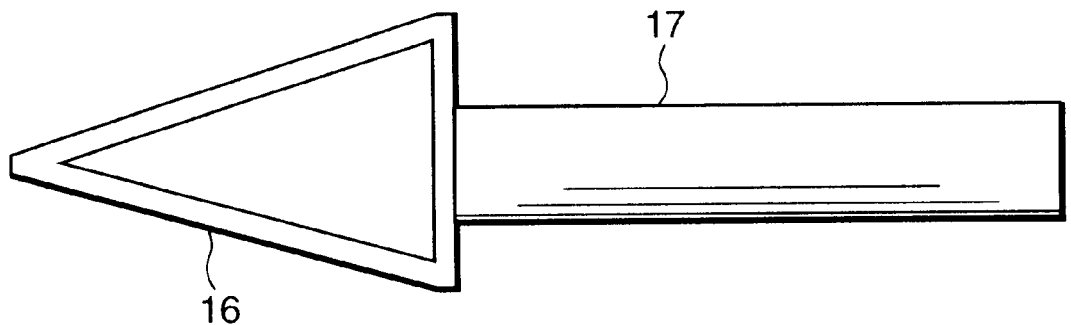
FIGS. 7A and 7B show embodiments of the retainer and arrow head of the present invention.
Figure 7B:
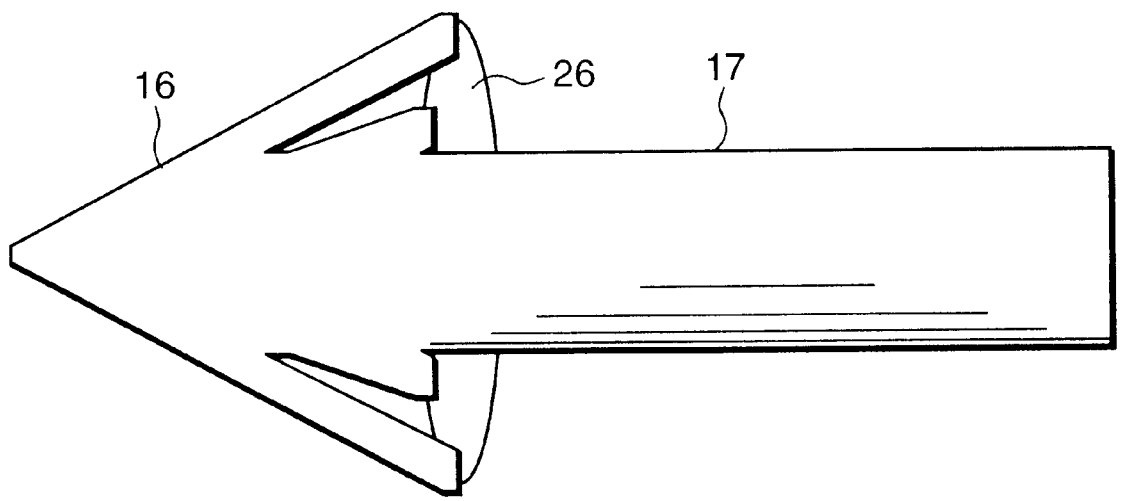

The arrow head 16 may be solid as seen in FIG. 7A. The arrow head 16 may also be constructed of a hollow outer cone 26 and an inner shaft 17 which is continuous with the elongate body 12. In this embodiment, the cone 26 collapses when passing through the tunnel 18 of the retainer 14 and returns to its original shape when the arrow head 16 is completely inserted through the tunnel 18 of the retainer 14 of the locking mechanism 20.

Figure 5:
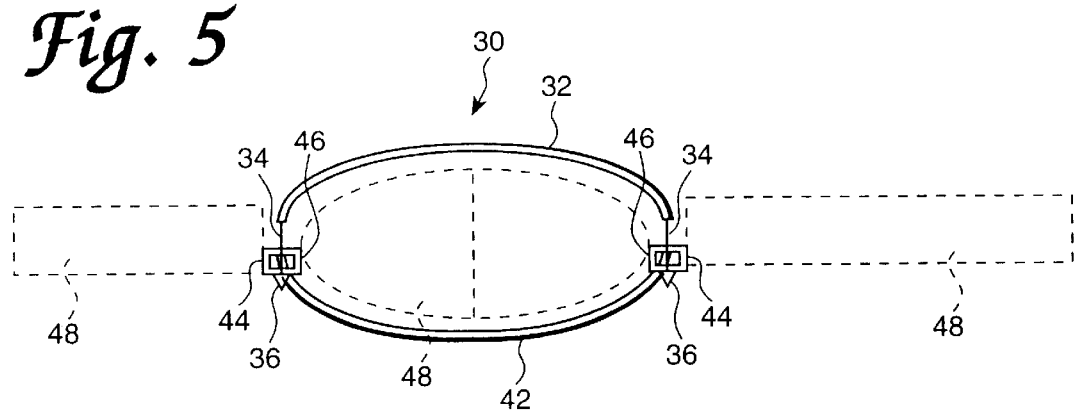
FIG. 5 shows one embodiment of the two-piece bioabsorbable staple of the present invention.

The second type of bioabsorbable staple is comprised of two pieces. The staple 30, seen in FIG. 5, has two parts. A first elongate body 32 has a leg 34 connected to an arrow head 36 at each end. The second elongate body 42 has a retainer 44 at each end. Each retainer 44 contains an eyelet 46, where each arrow head 36 of the first elongate body 32 engages with an eyelet 46 of the retainer 44 of the second elongate body 42. When the arrow heads 36 of the first elongate body 32 engage with the eyelets 46 of the retainer 44 of the second elongate body 42, an ellipsoid structure 30 is formed around the tissue 48 being closed.

In other words, the arrow heads 36 are separately inserted into the eyelets 46 of the retainers 44. Thus, the first arrow head 36 of the first elongate body 32 is inserted into the eyelet 46 of the first retainer 44 of the second elongate body 42. The second arrow head 36 of the first elongate body 32 is inserted into the eyelet 46 of the second retainer 44 of the second elongate body 42. The secured arrow heads 36, retainers 44, and elongate bodies 32 and 42 form a closed ellipsoid suture structure 30.

EXAMPLE 1

A one-piece bioabsorbable staple for tissue closure, especially for fascia closure, is made from polydiaxanone. The staple is fashioned to a pliable suture material with a diameter of, for example, #0, #1, or #2 and a length of, for example, 3 cm or 4 cm. The finished staple is double ended with a retainer at one end and an arrow head at the other end.

The staple is sterilized and used with a sterile self-contained delivery system. The staples are packed in packages of 10 to 50 staples per unit. The delivery system instrument is used to grasp and hold the tissue, e.g., fascia. The instrument is spring loaded and the delivery end of the instrument and handle resemble a pistol with a swivel barrel option. The staple is then forced through the tissue and locked into the retainer. Soft tissue tensioning is controlled by how much soft tissue is placed within the device. The inserted staple has an ellipsoid structure.

Thus, in this Example, the method comprises the steps of grasping and holding the tissue to be closed, forcing the one-piece bioabsorbable staple through the tissue, and locking the staple.

EXAMPLE 2

A two-piece bioabsorbable staple for tissue closure is made from copolymerized glycolic acid and lactic acid (polysorb). The piece of the staple is fashioned with a pliable suture material having a diameter of, for example, 0.5 to 0.6 mm, a staple width of 4.5 to 7 mm, and a staple leg length of, for example, 3 to 4 mm. The finished staple is made of an elongate body having a leg connected to an arrow head at each end and a second elongate body having a retainer with an eyelet at each end.

The staple is sterilized and used with a sterile self-contained delivery system. The staples are packed in packages of 10 to 50 staples per unit. The delivery system instrument is used to grasp and hold the tissue, e.g., fascia. The instrument is spring loaded and the delivery end of the instrument and handle resemble a pistol with a swivel barrel option. The staple is then forced through the tissue and locked into the retainer. Soft tissue tensioning is controlled by how much soft tissue is placed within the device. The inserted staple has an ellipsoid or curvilinear structure with convexity out for maximum purchase of soft tissue. Thus, in this Example, the method comprises the steps of grasping and holding the tissue to be closed, forcing the two-piece bioabsorbable staple through the tissue, and locking the staple.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A method for tissue closure, comprising the steps of:
   a) grasping and holding a tissue to be closed;
   b) forcing a one-piece bioabsorbable staple through said tissue, wherein said one-piece staple is comprised of:
      i) an elongate body, and
      ii) a locking mechanism, wherein said locking mechanism comprises a retainer having an enclosed central tunnel, said retainer located at a first end of said elongate body, and an arrow head located at a second end of said elongate body,
      wherein said staple forms an ellipsoid structure when said arrow head is inserted into said tunnel of said retainer of said locking mechanism; and
   c) locking said staple.

2. The method of claim 1, wherein said ellipsoid structure formed when said arrow head is inserted into said retainer of said locking mechanism has a smooth, tapered, and continuous outer surface, as seen in FIG. 3.

3. The method of claim 1, wherein said staple is constructed from polydiaxanone, a copolymer of glycolic acid and lactic acid, or from a blend of polydiaxanone and a copolymer of glycolic acid and lactic acid.

4. The method of claim 1, wherein said staple is constructed from polydiaxanone.

5. The method of claim 1, wherein said tissue is selected from the group consisting of fascia, tendon, muscle, and ligament.

6. The method of claim 1, wherein said tissue is fascia.

* * * * *